United States Patent [19]
Kato et al.

[11] Patent Number: 5,373,891
[45] Date of Patent: Dec. 20, 1994

[54] INVESTMENT MATERIAL AND MOLD FOR DENTAL USE AND BURNOUT THEREOF

[75] Inventors: Haruhisa Kato, Nagoya; Kiyoshi Mitsui, Toyoake, both of Japan

[73] Assignee: Noritake Co., Ltd., Nagoya, Japan

[21] Appl. No.: 866,901

[22] Filed: Apr. 6, 1992

[30] Foreign Application Priority Data

Apr. 30, 1991 [JP] Japan .................................. 3-128447
Apr. 30, 1991 [JP] Japan .................................. 3-128448

[51] Int. Cl.⁵ ................................................ B22C 1/00
[52] U.S. Cl. ...................................... 164/519; 106/35; 106/38.9
[58] Field of Search .................. 106/35, 38.9; 164/516, 164/517, 518, 519, DIG. 4

[56] References Cited
U.S. PATENT DOCUMENTS

| | | | |
|---|---|---|---|
| 4,604,142 | 8/1986 | Kamohara et al. | 164/520 |
| 4,814,011 | 3/1989 | Kamohara et al. | 106/35 |
| 4,909,847 | 3/1990 | Ohi et al. | 164/DIG. 4 |

FOREIGN PATENT DOCUMENTS

| | | |
|---|---|---|
| 2160689 | 6/1973 | France . |
| 54-39243 | 11/1979 | Japan . |
| 61-193741 | 8/1986 | Japan . |
| 2161155 | 1/1986 | United Kingdom . |
| 2187728 | 9/1987 | United Kingdom . |
| 2187729 | 9/1987 | United Kingdom . |
| 2198125 | 6/1988 | United Kingdom . |

OTHER PUBLICATIONS

Skinner et al., The Science of Dental Materials, 1991, 6th Ed. W. B. Saunders Company, USA, p. 425.
R&R Ultra-Vest Data Sheets (three pages), 1985.

*Primary Examiner*—P. Austin Bradley
*Assistant Examiner*—Erik R. Puknys
*Attorney, Agent, or Firm*—Frishauf, Holtz, Goodman & Woodward

[57] ABSTRACT

Dental investment materials for providing inexpensive dental investments which are free from the occurrence of cracks, crevices or breakage and can greatly reduce the metal casting time, dental casting molds using the same and a process for burning them. The dental investment material contains as the major components a calcined gypsum powder, a cristobalite powder and a quartz powder and additionally contains a gas permeability improving additive. In the dental investment prepared using such dental investment material, the thermal expansion can be dispersed and the steam pressure generated can be released effectively during calcination and burning.

13 Claims, 1 Drawing Sheet

INVESTMENT MATERIAL AND MOLD FOR DENTAL USE AND BURNOUT THEREOF

BACKGROUND OF THE INVENTION

This invention relates to a dental investment material for providing inexpensively a dental investment mold free from cracks, crevices or breakage even when it is subjected to rapid burnout and to a dental casting mold formed by using such dental investment material. This invention further relates to a process for burning out such dental investment, in which not only occurrence of cracks, crevices and breakage can securely be prevented but also metal casting operation time can greatly be reduced.

in the process of producing dental castings such as crowns, bridges and inlays, an investment material in which a wax pattern thereof is invested is used. After the investment material is set, the wax is eliminated by melting out and following the burning out process to provide a mold with a cavity of the same shape as that of the wax pattern. One of the important characteristics required for such investment materials is a degree of thermal expansion to compensate for shrinkage of cast metal to some extent in solidifying. Unlike the ordinary metal castings, it is difficult in the production of dental castings to produce a model having a slightly larger size than the actual tooth so as to compensate for such casting shrinkage in solidifying.

As the conventional dental investment materials for forming dental casting molds, a gypsum-cristobalite system investment material prepared by admixing cristobalite to a calcined gypsum and a gypsum-quartz system investment material prepared by admixing quartz to a calcined gypsum are widely utilized.

By the way, such types of dental casting molds are of a hollow body obtained by the molding of an investment material using a wax tooth model, and heating, followed by wax elimination. When a casting mold is prepared using thus obtained mold, it is burned out at a prescribed burnout temperature of about 700° C., and a molten alloy is casted therein. In this burnout process, it has conventionally been performed to heat the investment gradually from a low temperature such as about room temperature to a prescribed burnout temperature so as to prevent the investment from suffering from the occurrence of cracks, crevices or breakage. Accordingly, it takes a considerable time for such elevation of temperature. Further, the temperature of the furnace muse be lowered almost to normal temperature to start the next casting operation, requiring a great loss of time. Thus, the conventional investment materials suffer from extremely poor working efficiency, disadvantageously. Besides, since these investment materials cannot be subjected to rapid heating (to start heating at a high temperature or to heat at a high heating rate), they also suffer problems that they cannot cope with a case of emergency and that the life of furnace is shortened by the damage caused by the repeated heating/cooling cycle.

Details of such problems are described in Skinner's "The Science of Dental Materials", (1991) valued as a text of dental materials, as follows:

The rate at which the investment is heated is a factor in attaining a smooth surface on the casting. If heating is too rapid initially, the steam resulting from the elimination of the free water and water of crystallization may cause the walls of the mold to flake off as the steam emerges from the investment.

Too rapid heating may also cause cracking in the investment. In such a case, the outside layer of the investment becomes heated before the center portions. Consequently, the outside layer starts to expand thermally, resulting in compressive stress in the outside layer, counteracting tensile stress in the middle regions of the mold. Such a stress distribution causes the brittle investment to crack from the interior outwardly in the form of radial cracks. These cracks, in turn, will produce a casting with fins or spines similar to those shown in FIG. 23-7 of said Skinner's, "The Science of Dental Materials". This condition is especially likely to be present with a cristobalite investment. The comparatively low inversion temperature of the cristobalite, and the rapid rate of expansion during the inversion, make it especially important to heat the investment slowly.

SUMMARY OF THE INVENTION

This invention has been accomplished with a view to overcoming the problems inherent in prior art to provide a dental investment material for producing easily with high efficiency dental casting molds, free from cracks, crevices or breakage even when a rapid heating is applied, which can greatly reduce the metal casting time; the present dental investment material being capable of forming a mold immediately coping with a case of emergency, and besides requiring no cooling of the furnace to normal temperature after each cycle of the casting process, and also to provide a dental casting mold formed by use of such dental investment material.

It is another object of this invention to provide a process of burning out with high efficiency a dental investment, free from cracks, crevices or breakage even when rapid heating is applied by starting of burnout abruptly at an initial burnout temperature of 350° C. or higher, which can greatly reduce the metal casting time; the present dental investment material being capable of forming a mold immediately coping with a case of emergency, and besides requiring no cooling of the furnace to normal temperature after each cycle of the casting process.

The present dental investment material, having been provided with a view to overcoming the above problems contains a calcined gypsum powder, a cristobalite powder and a quartz powder, as major components, and characteristically contains additionally a gas permeability improving additive. The present dental investment mold containing a calcined gypsum powder, a cristobalite powder and a quartz powder, as the major components, and additionally a gas permeability improving additive is characterized in that it has a gas permeability of 0.04 cm/min or over.

The process of burning out the dental investment is characterized in that a dental investment containing a calcined gypsum powder, a cristobalite powder and a quartz powder, as the major components, can be burned out abruptly at an initial burnout temperature of 350° C. or higher, followed by further heating to a prescribed burnout temperature.

The calcined gypsum powder of the major components is used as a binder, while the cristobalite powder and quartz powder are used as refractory materials. It is not until the refractory cristobalite and quartz are admixed to the binder calcined gypsum that the thermal expansion during burnout can effectively be dispersed, enabling application of rapid heating which has been impossible in the prior art investment materials. Incidentally, the refractory cristobalite and quartz may be adjusted to have an average particle size of about 5 to 15 μm, respectively, so as to facilitate homogeneous mixing with the binder calcined gypsum. It is preferred that the calcined gypsum powder, cristobalite powder and quartz powder are incorporated in an amount of at least 20% by weight, respectively. If any of these major components is added in an amount of less than 20% by weight, dispersion of the thermal expansion may not sufficiently be effected, leading to the fear of crack, crevice or breakage formation when rapid heating is applied.

The gas permeability improving additive to be added to the major components of calcined gypsum powder, cristobalite powder and quartz powder is intended to give sufficient gas permeability to the mold so that the steam pressure accompanying the evaporation of the crystallined water and free water may effectively be released through the mold during calcination under rapid heating. The gas permeability improving additive also contribute effectively to the prevention of cracks, crevices or breakage formation by the steam pressure when rapid heating is applied.

As the gas permeability improving additive, at least one selected from the group consisting of inorganic salts such as calcium acrylate, potassium sulfate and sodium chloride; and refractories such as fused quartz powder, mullite powder and alumina powder is preferred. The gas permeability improving additive is added in an amount of, for example, not more than 10% by weight based on the amount of the major components. When a refractory is used as the gas permeability improving additive, one having an average particle size of greater than those of the cristobalite and quartz, e.g. about 20 to 30 μm, is preferred.

More specifically, when an inorganic salt is used as the gas permeability improving additive, it is added in an amount of 0.02 to 0.5% by weight, preferably 0.03 to 0.3% by weight based on the amount of the calcined gypsum. The addition of the inorganic salt is supposed to make the calcium sulfate dihydrate ($CaSO_4 \cdot 2H_2O$) crystalline particles, to be formed when a calcium sulfate hemihydrate ($CaSO_4 \cdot 1/2H_2O$) is set by addition of water, become bulky compared with a nonincorporated calcined gypsum, and these crystalline particles crowd one another during growth to provide greater crystal gaps therein and improve gas permeability of the set product.

Meanwhile, when a refractory powder is used as the gas permeability improving additive, one having an average particle size of greater than those of cristobalite and quartz. When the size of crystobalite or quartz is for example 5 to 15 μm, the size of the gas permeability improving additive is preferably 15 to 55 μm, more preferably 20 to 35 μm. The additive is added in an amount of, for example, about 10% by weight or less. Compared with cristobalite and quartz which undergo high levels of thermal expansion in the temperature ranges of 200° to 300° C. and 500° to 650° C., respectively, the refractory undergoes minor thermal expansion in these temperature ranges. Due to the presence of the refractory powder which undergoes very low thermal expansion and has a large average particle size induces crowding of the thermally expanded particles and unexpanded particles during heating. Accordingly, not only the gaps between the particles are enlarged to improve gas permeability of the set product, but also the effect of dispersing the thermal expansion is enhanced to prevent cracking effectively. In any case, a combination of materials which can give a set product having a gas permeability of at least 0.04 cm/min is preferred.

It is preferred that the refractory powder shows a thermal expansion behavior substantially different from those of cristobalite and quartz so that it can give gas permeability to the set product. The expression "a thermal expansion behavior substantially different from those of cristobalite and quartz" means, for example, that the total thermal expansion of the refractory in the temperature range of, for example, 20° to 700° C. is considerably lower than those of cristobalite and quartz. The refractory preferably shows a thermal expansion of 0.5% or less, more preferably 0.2% or less.

Now, referring to the production of a dental casting mold using the present dental investment material, for example, 20 to 40 parts by weight of water is added to 100 parts by weight of the dental investment material, and the resulting mixture is kneaded well, and, invested to a wax model in a casting ring. The wax is then eliminated to provide a dental casting mold having a cavity, to which a molten casting alloy is poured to form a desired castings such as a crown and a bridge in the same manner as has been practiced conventionally. However, the difference is that the present dental investment can be heated abruptly at an initial burnout temperature of not lower than 350° C. and rapidly heated, for example, to 700° C. with no cracks, crevices or breakage. One of the reasons is that the major components of the dental investment material consists of a combination of cristobalite and quartz as a refractory component in addition to the binder calcined gypsum, so that the thermal expansion during burnout can effectively be dispersed. A second reason is that the gas permeability improving additive also incorporated in the investment material allows the steam pressure accompanying the evaporation of the water contained in the material can effectively be released through the material. For example, as shown in FIG. 1, heating can be started abruptly at an initial burnout temperature of 350° C. (see Curve A), at 500° C. (see Curve B) or even at 700° C. (see Curve C). Thus, burnout time can greatly be reduced over the conventional method of starting calcination from normal temperature (see Curve S). The term initial burnout temperature used herein means a predetermined temperature to which the furnace is preheated before a green mold is placed therein.

The thus obtained dental investment has a gas permeability of 0.04 cm/min or more so as to release effectively the steam pressure generated during the process of calcination and also has extremely excellent surface properties including smoothness, with no cracks, crevices or breakage after burnout. Incidentally, gas permeability is determined by loading a test piece on an aeration table to which a differential manometer and a water tank are connected at each end portion to measure the amount of water discharged per unit time from the tank and the differential pressure and calculating according to the following equation:

Gas permeability (cm/min)=[Discharged water ($cm^3$)×Height of test piece (cm)]/[Section area of test piece ($cm^2$)×Differential pressure (cm)×Time (min)]

The dental investment to be used according to the process of burnout a dental investment can be obtained, for example, by adding 20 to 40 parts by weight of water to 100 parts by weight of a dental investment material, mixing the resulting mixture, and investing a wax model, followed by wax elimination in the same manner as has conventionally been practiced. However, the importance in this invention is that a dental investment material contains a calcined gypsum powder, a cristobalite powder and a quartz powder as the major components, and that burning, in which a molten alloy is poured into the cavity of the mold to obtain a desired castings such as a crown and a bridge, can be started abruptly at an initial burnout temperature of 350° C. or higher and heated rapidly to a prescribed burnout temperature of, for example, 700° C.

Examples of temperature curves from the initial burnout temperature to a prescribed burnout temperature are as shown in FIG. 1. Thus, heating can be started at an initial temperature of 350° C. (Curve A), followed by heating rapidly to the prescribed burnout temperature of 700° C., and at this temperature the dental investment molds are heated for about 30 minutes. The initial burnout temperature can arbitrarily be selected within the range of 350° to 700° C., and the burnout operation can be started, for example, at 500° C. as shown by Curve B or at the prescribed burnout temperature of 700° C. from the beginning as shown by Curve C. In any case, the burnout time is drastically reduced over Curve S in which burnout operation is started from normal temperature as conventionally practiced.

The dental investment material for the dental casting mold to be used according to this invention contains as the major components refractory cristobalite and quartz in addition to the binder calcined gypsum, and such composition can effectively disperse the thermal expansion during burnout operation to securely prevent occurrence of cracks, crevices or breakage. Accordingly, the resulting dental casting mold involves no problem in the quality. The addition of a gas permeability increasing additive to the major components is also preferred, and if such is the case, a casting mold having further excellent quality can be obtained, since the steam pressure accompanying the evaporation of the water contained in the investment material can effectively be released therethrough.

The reason for the admixing of cristobalite and quartz as the refractories to the binder calcined gypsum is to achieve effective dispersion of the thermal expansion during burning operation, so that the burning operation can be started abruptly at an initial burnout temperature of 350° C. or higher. Incidentally, as the refractory cristobalite and quartz, those having an average particle size of about 5 to 15 μm, respectively, are used so as to facilitate homogeneous mixing with the binder calcined gypsum. The calcined gypsum, cristobalite and quartz powders are preferably incorporated in an amount of at least 20% by weight, respectively. If any of these major components is added in an amount of less than 20% by weight, dispersion of the thermal expansion may not sufficiently be carried out, and cracks, crevices or breakage is liable to occur when the resulting investment mold is subjected to heating abruptly at an initial burnout temperature of 350° C. or higher.

As described above, it is also possible to add a gas permeability improving additive to the major components. If such gas permeability improving additive is incorporated, it can impart sufficient gas permeability to the resulting investment so as to allow the steam pressure accompanying the evaporation of the crystallined water and free water to escape therethrough and in turn prevent effectively occurrence of cracks, crevices or breakage, when the investment is subjected to rapid heating at an initial burnout temperature of 350° C. or higher.

DESCRIPTION OF THE PREFERRED EMBODIMENTS

Example 1

Figure 1:
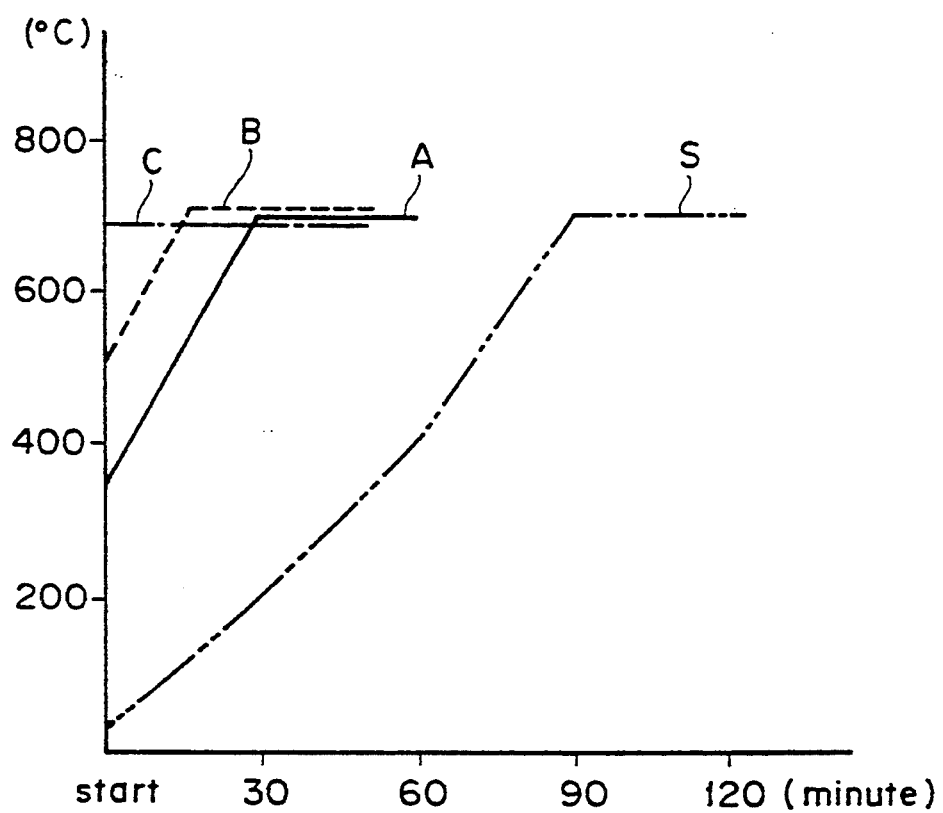
FIG. 1 is a graph showing temperature curves in the burnout process.

To 100 parts by weight of the dental investment material consisting of a calcined gypsum, a cristobalite and a quartz as the major components, as shown in Table 1, was added 5 parts by weight of a gas permeability improving additive, and the consistency (water content) was adjusted to 33%, followed by kneading. A wax tooth model was invested by the kneaded mixture to form a dental casting mold. Subsequently, thus obtained dental investment mold was subjected to rapid heating to 700° C. from an initial burnout temperature of 500° C., followed by casting of a molten alloy to the cavity of the mold formed after elimination of the wax tooth model to give a desired castings.

The dental investment molds obtained as described above all were of high quality, since they were free from crack, crevice or breakage and had very excellent surface properties as well as smoothness.

TABLE 1

| Example | 1 | 2 | 3 | 4 | 5 | 6 |
| --- | --- | --- | --- | --- | --- | --- |
| Basic component | | | | | | |
| Calcined gypsum | 30 | 30 | 30 | 30 | 30 | 30 |
| Cristobalite (av. φ: 10 μm) | 50 | 40 | 35 | 30 | 25 | 20 |
| Quartz (av. φ: 6 μm) | 20 | 30 | 35 | 40 | 45 | 50 |
| Gas permeability improving additive | | | | | | |
| Potassium sulfate | — | 0.15 | 0.1 | — | 0.1 | 0.15 |
| Calcium acrylate | 0.2 | — | — | 0.2 | — | — |
| Fused silica (quartz) (av. φ: 20 μm) | — | — | — | 5.0 | — | — |
| Mullite (av. φ: 25 μm) | — | 5.0 | — | — | 5.0 | — |
| Initial burnout temperature (°C.) | 350 | 500 | 700 | 350 | 500 | 700 |
| Mold | | | | | | |
| Crack etc. | none | none | none | none | none | none |
| Gas permeability (cm/min) | 0.04 | 0.08 | 0.05 | 0.06 | 0.07 | 0.06 |

Example 2

To 100 parts by weight of the basic formulation consisting of a calcined gypsum, a cristobalite and a quartz as the major components, as shown in Table 1, was added 5 parts by weight of a gas permeability improving additive together with water, and the consistency was adjusted to 33%, followed by kneading. A wax tooth model was invested by the kneaded mixture to form a dental investment mold. Subsequently, thus obtained dental investment mold was subjected to rapid heating to 700° C. from an initial burnout temperature of 350° C. or higher, followed by casting of a molten alloy to the cavity of the mold formed after elimination of the wax tooth model to give a desired castings.

The dental investment molds obtained as described above all were of high quality, since they were free from cracks, crevices or breakage and had very excellent surface properties including smoothness.

As has been describe above, the dental investment material according to a first aspect of this invention can facilitate formation of a dental investment free from cracks, crevices or breakage by conventional procedure even if it is subjected to rapid heating. Meanwhile, the present dental investment mold is free from cracks, crevices or breakage even if rapid heating is applied, so that the metal casting time can greatly be reduced. Further, the present dental investment mold can immediately cope with a case of emergency. Since the burning is started at a high temperature, the furnace need not be cooled to normal temperature after each cycle of casting process, enhancing working efficiency and in turn contributing to energy saving. Besides, the present dental casting mold according to a second aspect of this invention enjoys many advantages including that it can provide a castings with excellent quality having smooth surface with no cracks, crevices and breakage.

Accordingly, the present dental investment material and dental investment mold having overcome the prior art problem contribute much to the development of the industry.

In the process of heating the dental investment mold according to a third aspect of this invention, rapid heating can be applied by starting calcination abruptly at an initial burnout temperature of 350° C. or higher with no occurrence of cracks, crevices or breakage. Accordingly, not only the metal casting time can greatly be reduced, but also a castings can immediately be formed coping with a case of emergency. In addition, the furnace need not be cooled to normal temperature after each cycle of casting process, and thus working efficiency can be improved. The present process also enjoys an advantage that if the furnace constantly set at a prescribed burnout temperature, casting can be carried out at any time with no loss time.

As has been described heretofore, this invention having overcome the prior art problems can reduce not only the cost of burning operation, by a large margin, but also the production cost, since the calcined gypsum, cristobalite and quartz powders used as the major components of the present dental investment material for dental casting molds are not expensive materials, contributing greatly to the development of the industry.

What is claimed is:

1. A dental investment material comprising a calcined gypsum powder, a crystobalite powder, a quartz powder and a gas permeability improving additive, wherein the gas permeability improving agent comprises refractory powders having an average particle size of at least 1.5 times greater than the average particle size of the cristobalite powder and the quartz powder and also having a thermal expansion behavior different from the thermal expansion behavior of the cristobalite powder and the quartz powder; the cristobalite powder and the quartz powder each having an average particle size of 5 to 15 μm; the calcined gypsum powder, the cristobalite powder and the quartz powder are each contained in an amount of at least 20% by weight; and the gas permeability improving additive providing a gas permeability of 0.04 cm/minute or more for the dental investment material.

2. The dental investment material according to claim 1, wherein the refractory powders have a thermal expansion of 0.5% or less in the temperature range of 20° to 700° C.

3. The dental investment material according to claim 1, wherein the refractory powders have a thermal expansion of 0.2% or less in the temperature range of 20° to 700° C.

4. A dental casting mold made of the dental investment material as claimed in claim 1 and defining a tooth-shaped hollow cavity.

5. A dental investment material comprising a calcined gypsum powder, a cristobalite powder, a quartz powder and a gas permeability improving additive, the gas permeability additive is a refractory having an average particle size of 20 to 30 μm; the cristobalite powder and the quartz powder each having an average particle size of 5 to 15 μm; the calcined gypsum powder, the cristobalite powder and the quartz powder are each contained in an amount of at least 20% by weight; and the gas permeability improving additive providing a gas permeability of 0.04 cm/minute or more for the dental investment material.

6. The dental investment material according to claim 5, wherein the gas permeability additive is in an amount of not more than 10% by weight based on the amounts of the gypsum powder, the cristobalite powder and the quartz powder.

7. A dental casting mold made of the dental investment material as claimed in claim 5 and defining a tooth-shaped hollow cavity.

8. A dental investment material comprising a calcined gypsum powder, a cristobalite powder, a quartz powder and a gas permeability improving additive, the gas permeability additive has an average particle size of 15 to 55 μm; the cristobalite powder and the quartz powder each having an average particle size of 5 to 15 μm, the calcined gypsum powder, the cristobalite powder and the quartz powder are each contained in an amount of at least 20% by weight; and the gas permeability improving additive providing a gas permeability of 0.04 cm/minute or more for the dental investment material.

9. The dental investment material according to claim 8, wherein the gas permeability additive has an average particle size of 20 to 35 μm.

10. A dental casting mold made of the dental investment material as claimed in claim 8 and defining a tooth-shaped hollow cavity.

11. The process of burning a dental investment according to claim 8, wherein the dental investment further comprises at least one gas permeability improving additive selected from the group consisting of (i) inorganic salts selected from the group consisting of calcium acrylate, potassium sulfate and sodium chloride, and (ii) a refractory selected from the group consisting of a fused quartz powder, a mullite powder and an alumina powder.

12. A process of burning a dental investment material, said dental investment material comprising a calcined gypsum powder, a cristobalite powder, a quartz powder and a gas permeability improving additive, the cristobalite powder and the quartz powder each having an average particle size of 5 to 15 μm; the calcined gypsum powder, the cristobalite powder and the quartz powder are each contained in an amount of at least 20% by weight; and the gas permeability improving additive having an average particle size of 15 to 55 μm and providing a gas permeability of 0.04 cm/minute or more for the dental investment material, the method comprising subjecting the dental investment material to a burnout at an initial burnout temperature of 350° C. or higher, followed by heating further to 700° C.

13. The process of burning a dental investment according to claim 12, wherein the dental investment further comprises at least one gas permeability improving additive is selected from the group consisting of (i) inorganic salts selected from the group consisting of calcium acrylate, potassium sulfate and sodium chloride, and (ii) a refractory selected from the group consisting of a fused quartz powder, a mullite powder, and an alumina powder.

* * * * *